US009719778B2

(12) United States Patent
Leconte et al.

(10) Patent No.: US 9,719,778 B2
(45) Date of Patent: Aug. 1, 2017

(54) METHOD AND DEVICE FOR MEASURING THE VERTICALITY OF A CONTAINER

(75) Inventors: Marc Leconte, Loire sur Rhone (FR); Jean-François Garin, Saint-Romain en Gal (FR)

(73) Assignee: MSC & SGCC, Vourles (FR)

( * ) Notice: Subject to any disclaimer, the term of this patent is extended or adjusted under 35 U.S.C. 154(b) by 922 days.

(21) Appl. No.: 14/008,701

(22) PCT Filed: Mar. 28, 2012

(86) PCT No.: PCT/FR2012/050646
§ 371 (c)(1),
(2), (4) Date: Dec. 6, 2013

(87) PCT Pub. No.: WO2012/131251
PCT Pub. Date: Oct. 4, 2012

(65) Prior Publication Data
US 2014/0088916 A1  Mar. 27, 2014

(30) Foreign Application Priority Data
Mar. 30, 2011 (FR) ...................................... 11 52658

(51) Int. Cl.
*G01B 21/02* (2006.01)
*G01B 11/00* (2006.01)
(Continued)

(52) U.S. Cl.
CPC .............. *G01B 21/02* (2013.01); *G01B 11/26* (2013.01); *G01N 21/90* (2013.01); *G01B 11/002* (2013.01)

(58) Field of Classification Search
CPC ...................................................... G01N 21/90
(Continued)

(56) References Cited

U.S. PATENT DOCUMENTS

| 4,433,785 A | 2/1984 | Riggs et al. |
| 4,906,098 A * | 3/1990 | Thomas ................. G01B 11/24 |
| | | 209/525 |

(Continued)

FOREIGN PATENT DOCUMENTS

| EP | 0 341 849 | 11/1989 |
| FR | 2 314 474 | 1/1977 |
| JP | 2005-091060 | 4/2005 |

*Primary Examiner* — Gregory J Toatley
*Assistant Examiner* — Terence Stifter, Jr.
(74) *Attorney, Agent, or Firm* — Clark & Brody

(57) ABSTRACT

A method for measuring verticality of a container having a base and vertical wall comprises measuring at each rotational position of the container, at least the position along a first measurement axis, of at least one first measuring point located on the base, and a second measuring point located on the base diametrically opposite to the first measuring point, the position along a third measurement axis, of at least one third measuring point located on the vertical wall at a distance from the base. An angle defined between a first segment passing through the first and second measuring points and a second segment intersecting the first segment and passing through at least the third measuring point is selected to be representative of the container verticality. For each rotational position of the container, a quantity depending on the angle is calculated. Verticality is measured from the variations of the calculated quantity.

17 Claims, 3 Drawing Sheets

(51) Int. Cl.
*G01B 11/26* (2006.01)
*G01N 21/90* (2006.01)

(58) Field of Classification Search
USPC .......................................................... 702/155
See application file for complete search history.

(56) References Cited

U.S. PATENT DOCUMENTS

| | | | | |
|---|---|---|---|---|
| 6,212,962 B1* | 4/2001 | Lucas | ................... | B07C 5/3408 |
| | | | | 73/865.8 |
| 7,010,863 B1* | 3/2006 | Juvinall | ................. | G01B 11/26 |
| | | | | 33/522 |
| 7,480,040 B2* | 1/2009 | Juvinall | ................. | G01N 21/90 |
| | | | | 356/239.4 |
| 2006/0192954 A1 | 8/2006 | Semersky et al. | | |

* cited by examiner

METHOD AND DEVICE FOR MEASURING THE VERTICALITY OF A CONTAINER

The present invention relates to the technical field of inspection of hollow objects or containers in the general sense, such as for example, bottles, pots, flasks notably glass flasks with view to conducting measurements of the verticality of such containers.

In the technical field of inspection of containers, notably glass containers, such as bottles, the need arises for measuring the verticality of the containers, in order to in particular guarantee their bottling or their conditioning. It should be noted that in the state of the art, the verticality of a container is expressed in various ways. For example, the verticality of a container is expressed in the form of an angle or a degree of tilt. Expressing verticality as the deviation between the center of the base of the container and the center of a cross-section of the container taken according to a selected height of the container, such as the ring for example, is also known. Instead of taking into account the difference between the centers of the two sections of the container, verticality is also considered as the measurement of the radial excursion over one revolution of a point of the container taken at a relevant height of the container.

Regardless of how verticality is expressed, the measurement of verticality of a container gives important information on the dimensional characteristics of a container with which it is for example possible to detect its lack of verticality when the measurement exceeds a reference value. In the state of the art, many technical solutions have been proposed for measuring verticality of bottles.

For example, U.S. Pat. No. 4,433,785 describes a detection system including two free wheels in contact with the base of the bottle. During the rotation of the container in an inspection station, the vertical displacements of both of the wheels are measured by means of electromagnetic position sensors. Such a system is not suitable for high throughput control due to the risk of losing the contact of the free wheels with the base of the bottles. Moreover, such a system cannot give an accurate measurement and has an obvious risk of wear. More fundamentally, this system only measures the movements of the base of the bottle relatively to the axis of rotation, imposed by the inspection station. In fact, when the container for example has deformations on the body, it no longer rotates around its axis of symmetry so that the measurement of verticality is erroneous.

U.S. Pat. No. 7,010,863 describes another technique consisting of replacing both free wheels with two optical measurement sensors giving the possibility of directing light in two points of the base of the bottle lying on a support plane. From the light reflected by the bottle and from the rotation of the bottle, the deviation between the support plane and a plane perpendicular to the axis of rotation is determined in order to infer a lack of verticality therefrom. With such a device it is possible to suppress the drawbacks related to the use of free wheels. However, the measurement principle of such a device is based on the assumption that the container is perfect in every point except for the base which is tilted. This assumption leads to the consideration that the central axis of the container coincides with the axis of rotation of the inspection station so that it is sufficient to measure the displacements of the base of the container. Now, in practice, the axis of the container does not coincide with the axis of rotation of the inspection station. Also, the prior art does not give the possibility of obtaining a real measurement of the verticality of a container. Additionally, the known prior solutions do not give the possibility of measuring the verticality of the neck of such containers.

Moreover, patent application EP 0 341 849 describes a method for measuring the profile and the verticality of a container having a base from which rises a vertical wall. The container is freely laid on a supporting plane which is driven into rotation so as to allow measurements to be conducted over the whole periphery of the container. The supporting plane of the container is used as a reference plane for the measurement of verticality. Now, in the field of industrial measurements, verticality measurements conducted from a reference taken on the handling system are not reliable. Such is notably the case for measuring the verticality of containers on a rotating station located on a manufacturing line. Indeed such a rotating monitoring station includes a support plane for the container and a system for driving the container into rotation, consisting of a wheel for driving into rotation the container which is found placed and bearing upon at least two abutments during its rotation. The axis of rotation of the container constantly varies so that the movement is random and unpredictable. Moreover, it proves to be impossible to place the base of the container in the reference plane formed by the support plane in particular taking into account the non-circular section of the containers (made oval or with flats), the presence of lame bases, deformation of the container and defects affecting the system for rotating the container.

U.S. Pat. No. 6,212,962 also describes a device for inspecting containers translationally running past them, in particular intended for determining the tilt of the body of the container relatively to its base. Such a device does not give the possibility of detecting a lack of verticality in the case when the article would for example exhibit deformation of its wall at the measurement height of a reference product. Thus, a recess, flat or ovalization at a given height would erroneously lead to considering the article as tilted.

The present invention therefore aims at finding a remedy to the drawbacks of the state of the art by proposing a novel technique giving the possibility of measuring the actual verticality exhibited by containers, these measurements being conducted on the manufacturing line by a rotating station for allowing measurements over the whole periphery of the containers.

In order to attain such a goal, the object of the invention proposes a method for measuring the verticality of a container having a base from which rises a vertical wall, the method consisting of rotating the container on itself over at least one revolution and of conducting during the rotation of the container, measurements at different rotational positions of the container.

The latter consists of:
measuring at each rotational position of the container, at least:
the position along a first measurement axis, of at least one first measuring point located on the base,
the position according to a second measurement axis, of a second measuring point located on the base diametrically opposite to the first measuring point,
the position according to a third measurement axis, of at least one third measuring point located on the vertical wall at a distance from the base, the first, second and third measurement axes being coplanar in a measurement plane,
selecting an angle defined between a first segment passing through the first and second measuring point and a second segment intersecting the first segment and passing at least through the third measuring point so that the variation of this angle is representative of the verticality of the container, calculating for each rotational position of the container, a quantity depending on the angle, and measuring the verticality from the variations of the quantity depending on this angle, considered over at least one revolution of the container.

The method according to the invention provides the advantage of being able to measure the actual verticality of the containers, independently of the handling conditions of the inspection station, thus giving the possibility of doing without the rotation of the container around a non-vertical axis, without the upward movement of the container during the inspection or without the ovalization exhibited by the container.

The method according to the invention further includes as a combination, either one or both of the following additional features:

measuring the verticality by calculating the difference between the maximum value and the minimum value of the quantity depending on the angle, measuring the verticality, after an operation for filtering variations of the quantity depending on the angle, selecting the angle defined between the first segment and the second segment passing through the third measuring point and the first measuring point, measuring in each rotational position of the container, the position along at least one fourth measurement axis or even a fifth measurement axis coplanar with the first, second and third measurement axes, of at least one fourth measuring point or even a fifth measuring point located on the vertical wall of the container in different locations of the third measuring point, selecting the positions of the third and fourth measuring point on the vertical wall located on the body as far as possible from the base, and on the ring of the container, so as to define an angle defined between the first segment and the second segment passing through the third and first measuring point and another angle defined between the first segment and the second segment passing through the fourth and first measuring points allowing definition of a verticality measurement of the body for the point located on the body and a complete verticality measurement for the point located on the ring, selecting at least one angle defined between the first segment and the second segment passing through the third measuring point and the fourth measuring point located in proximity to the heel, selecting the position of the third measuring point on the body as far as possible from the base in order to determine a body verticality measurement and selecting the position of the fifth measuring point on the ring of the container so as to define another angle defined between the first segment and the second segment passing through the fourth and fifth measuring points allowing definition of a complete verticality measurement, determining a verticality measurement of the neck relatively to the body from the difference between the complete and body verticality measurements, calculating, for each rotational position of the container, as a quantity depending on the angle $\alpha$ defined by the first, second and third measuring points or defined by the first, second and fourth measuring points, the deviation between the angles $\alpha_1$ and $\alpha_2$ or the deviation between the tangents of angles $\alpha_1$ and $\alpha_2$, with:

$\alpha_1$ being the tilt angle between the segment passing through the first and second measuring point and a segment parallel with the first axis parallel to the third measurement axis and being part of an orthonormal reference system located in the measurement plane, and $\alpha_2$ being the tilt angle between the segment either passing through the first and third or fourth measuring points or through the third and fourth measuring points and a segment parallel with the second axis parallel to the first and second measurement axes and being part of the orthonormal reference system, referencing to a zero value, the positions measured by the sensors, comparing the verticality measurement with a reference value for determining the presence of a lack of verticality or not, measuring the position of the different measuring points by means of sensors in contact or without contact with the container, measuring the position of the different measuring points by means of contactless sensors of the optical type.

Another object of the invention is to propose a device for measuring the verticality on containers having a base from which rises a vertical wall, each container being driven into rotation on itself according to at least one revolution, the device including a measurement system connected to a processing and computing unit.

The measurement system includes at least three measurement sensors suitable for measuring the position along first, second and third measurement axes coplanar with each other, of first, second and third measuring points, the first and the second measuring points being located on the base of the container diametrically opposite to each other while the third measuring point is located on the vertical wall at a distance from the base, the processing and calculation unit including means for calculating, for each rotational position of the container, a quantity depending on an angle defined between a first segment passing through the first and second measuring points and a second segment intersecting the first segment and passing through at least the third measuring point so that the variation of this angle is representative of the verticality of the container, this processing and calculation unit including means for determining a measurement of verticality from variations of the quantity depending on this angle.

The device according to the invention includes as a combination either one or both of the following additional features:

the measurement system includes at least one fourth measurement sensor suitable for measuring the position, at each rotational position of the container, along a fourth measurement axis coplanar with the first, second and third measurement axis, of a fourth measuring point located on the vertical wall of the container and in that the processing and calculation unit includes means for calculating, for each rotational position of the container, a quantity depending on at least one angle defined by the first segment and the second segment either passing through the third and first measuring points or through the third and fourth measuring points, the processing and calculating unit including means for determining at least one measurement of verticality from the variations of the quantity depending on this angle, the sensors are contactless sensors of the optical type.

Various other features will become apparent from the description made below with reference to the appended drawings which show, as non-limiting examples, embodiments of the object of the invention.

Figure 1:
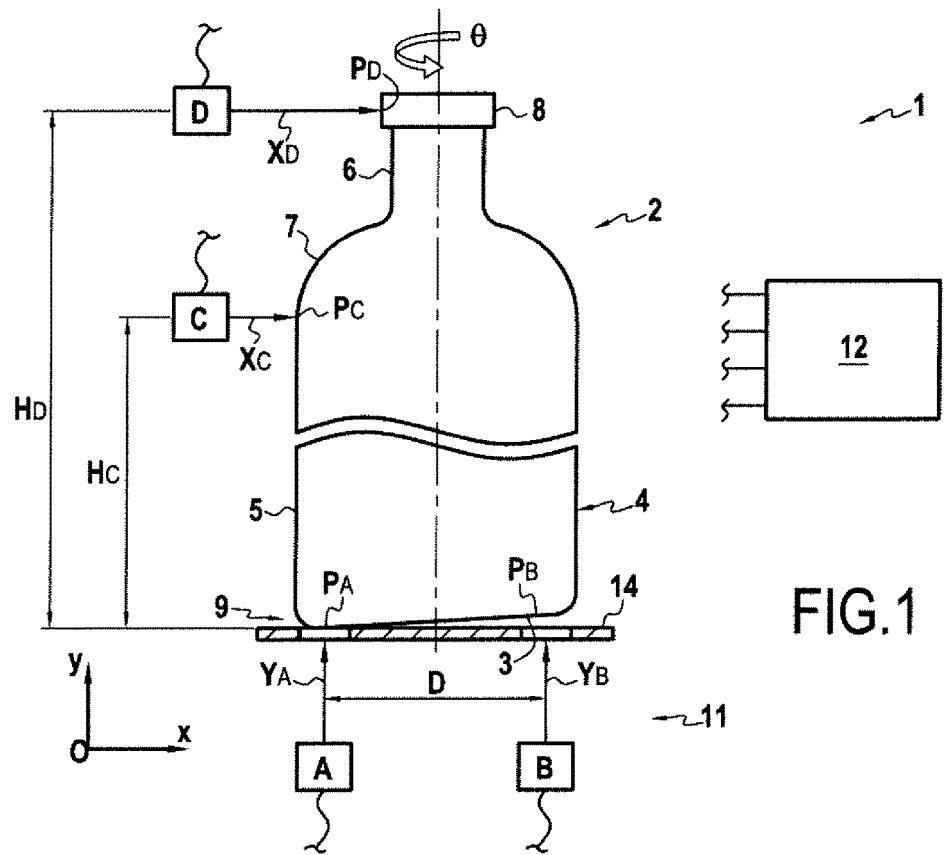
FIG. 1 is an elevational sectional view of a diagram illustrating a detection device according to the invention.
Figure 2:
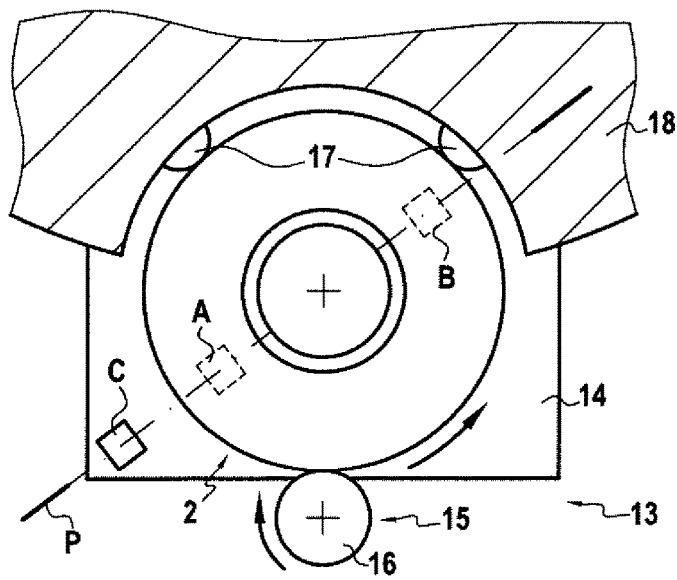
FIG. 2 is a top view of the detection device according to the invention.

As this becomes more specifically apparent from FIGS. 1 and 2, the object of the invention relates to a device 1 for measuring the verticality on containers 2 for example in glass such as bottles. Conventionally, each container 2 has a base 3 from which rises a vertical wall 4. In the case of a container of the bottle type, the vertical wall 4 exhibits from the base 3, a portion 5 forming the body of the bottle which is connected to a neck 6 via a shoulder 7. The neck 6 ends with a so-called ring or neck portion 8. By contrast, the body 5 of container 2 is connected to the base 3 through a heel or head 9.

The detection device 1 includes a measurement system 11 connected to a processing and calculation unit 12 allowing determination of the verticality measurement of the bottle 2.

The verticality measurement of a container 2 is conducted while the container 2 is set into rotation on itself (angle θ) according to at least one revolution. In this respect, each container 2 is managed by a driving system 13. For example, the driving system 13 includes a sliding or supporting plane 14 for the base 3 of the container 2 as well as a rotary drive system 15 including a wheel or whirler 16 for driving into rotation the container secured by its body 5 bearing upon two abutments 17 during its rotation on itself. Both abutments 17 are, for example, part of a star 18 for handling, giving the possibility of successively bringing the containers 2 in front of the measurement system 11. Each container 2 remains in front of the detection device 1 for the required time in order to perform at least one revolution on itself during which measurements are conducted as this will be explained subsequently in the description. The drive 13 and rotary drive systems 15 are not described more specifically since they are not part of the object of the invention and are well known to the person skilled in the art. It should be considered that the rotary drive system 15 is not capable of placing the containers 2 in a reproducible fixed position relatively to the detection device 1 and in particular on the sliding plane 14. Thus, as illustrated in FIG. 1, the base 3 of the container may not be entirely bearing upon the sliding plane 14 during the rotation of the container.

The measurement system 11 includes at least three measurement sensors and according to an alternative embodiment illustrated in FIG. 1, four measurement sensors A, B, C, D mounted in a fixed and known way relatively to the support plane 14. The measurement system 11 includes a first measurement sensor A and a second measurement sensor B suitable for measuring the position according to first YA and second YB measurement axes respectively of first PA and second PB measuring points located on the container 2. Thus, each measuring point PA, PB corresponds to a point of the external surface of the container 2 located on the relevant measurement axis.

The first measuring point PA and the second measuring point PB are located on the base 3 of the container while being positioned diametrically opposite in a measurement plane P. The first sensor A is capable of measuring the position of a first point PA of the base 3 of the container, relatively to the first sensor A and along the measurement axis YA. Also, the second sensor B is capable of measuring the position of a second point PB of the base 3 relatively to the second sensor B and along the measurement axis YB.

The first measurement axis YA and the second measurement axis YB substantially extend parallel with each other and with an axis y being part of a orthonormal reference system (0, x, y) located in the measurement plane P and including a first axis x and a second axis y perpendicular to each other. The first YA and second YB measurement axes are separated from each other by a known distance D.

According to a feature of the invention, the measurement system 11 necessarily includes at least one third measurement sensor C suitable for measuring the position of a third measuring point PC located on the vertical wall 4 of the container 2 at a distance from the base 3 and along a third measurement axis XC. This third measurement axis XC and the first YA and second YB measurement axes are coplanar in the measurement plane P. This third measurement axis XC is parallel to the first axis x which is part of the orthonormal reference system (0, x, y). The third measurement axis XC may advantageously be located either on the body 5 at the shoulder 7, or on the neck 6 or on the ring 8.

The positioning of the third measurement axis XC to a determined level of the vertical wall 4 allows measurement of the verticality at this measurement axis. For example, the positioning of the third measurement axis XC in proximity to the shoulder 7 allows, as this will be described more specifically in the continuation of the description, determination of a measurement of verticality at the body 5 of the container 2. Also, the positioning of the third measurement axis XC at the ring 8 allows determination of a measurement of verticality at the ring 8 of the container.

According to the alternative illustrated in FIG. 1, the measurement system 11 includes a third sensor C, the measurement axis XC (third measurement axis) of which is located on the body 5 at the shoulder 7, and a fourth sensor D, the measurement axis XD (fourth measurement axis) of which is located at the ring 8. According to this advantageous alternative embodiment, a measurement of verticality of the neck 6 may be determined by taking into account the difference between the verticality measurement of the ring 8 and the verticality measurement of the body 5.

According to a first alternative embodiment illustrated in FIG. 1, the measurement system 11 includes four sensors by considering that the third sensor corresponds to the sensor C with a measurement axis XC located on the body 5 at the shoulder 7 while the fourth sensor is the sensor D located at the ring 8 with a measurement axis XD. Of course, provision may be made for inverting the positions between the third and fourth sensors.

The third measurement sensor C and the fourth measurement sensor D are suitable for measuring the positions along third XC and fourth XD measurement axes respectively, of third PC and fourth PD measuring points located on the container 2. Each measuring point PC, PD corresponds to a point of the external surface of the container 2 located on the relevant measurement axis. In the relevant example, the third measuring point PC is located on the body 5 of the container in proximity to the shoulder 7 while the fourth measuring point PD is located on the ring 8 of the container 2. The third measurement axis XC and the fourth measurement axis XD substantially extend parallel with each other and with the first axis x of the orthonormal reference system (0, x, y). The first YA, second YB, third XC and fourth XD measurement axes are coplanar with each other in the measurement plane P. The third measurement axis XC is distant from the support plane 14 by a known distance HC while the fourth measurement axis XD is distant from the support plane 14 by a known value HD.

The sensors A to D are suitable for contact or contactless measurement of the position of the points PA to PD located on the facing container, along coplanar measurement axes YA, YB, XC, XD, respectively. According to a third alternative embodiment, the measurement sensors are of the contactless type. According to an advantageous alternative embodiment, the measurement sensors A to D are contactless measurement sensors of the optical type.

The measurement sensors A to D are connected to a processing and calculation unit 12 allowing determination of the verticality measurement of the containers 2. In this respect, the processing and acquisition unit 12 makes an acquisition of the measurements conducted by at least three and in the illustrated example, the three sensors A to D at each rotational position or increment of the container 2 and this, for at least one revolution of the container 2. Thus, a step or a rotary increment is selected so that for each value of rotation θ of the container 2, the processing and calculation unit 12 acquires measurements from at least three sensors and in the illustrated example from the four sensors A to D. For example, it is possible to select a rotational increment of 1 mm leading for a given container to the acquisition, for one revolution of the container, of about a hundred acquisitions of measurements, each of the acquisitions including the measurements of the four sensors A to D.

The processing and calculation unit 12 calculates for each rotational position or increment of the container 2, at least one quantity depending on angle α defined between a first segment $x_1$ passing through the first PA and second PB measuring points and a second segment $x_2$ intersecting the first segment $x_1$ and passing through at least the third measuring point PC so that the variation of this angle α is representative of the verticality of the container 2.

Figure 3:
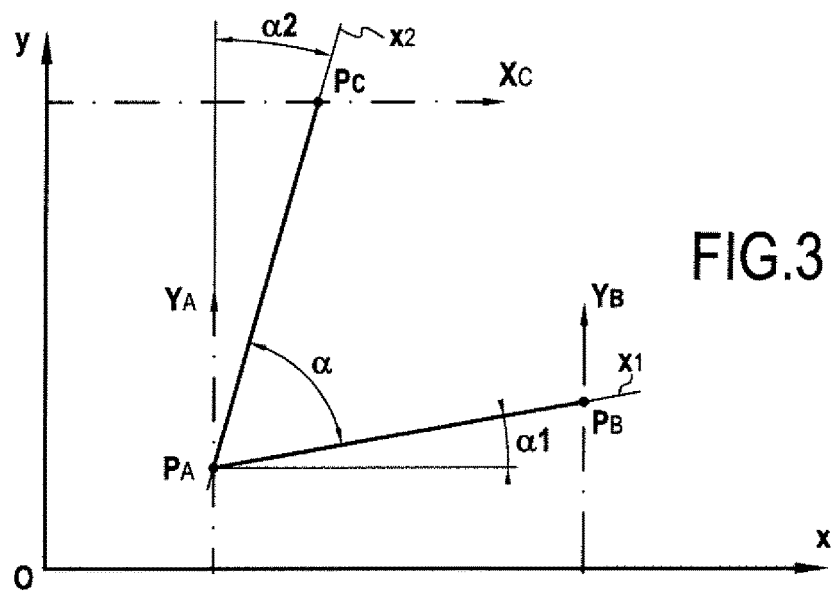
FIG. 3 is a diagram illustrating the principle of the invention according to a first alternative embodiment.

According to a first alternative embodiment, the angle α is defined between the first segment $x_1$ and the second segment $x_2$ which passes through the third measuring point PC and the first measuring point PA (FIG. 3). According to this first alternative, the segments $x_1$ and $x_2$ intersect at the first measuring point PA.

Figure 5:
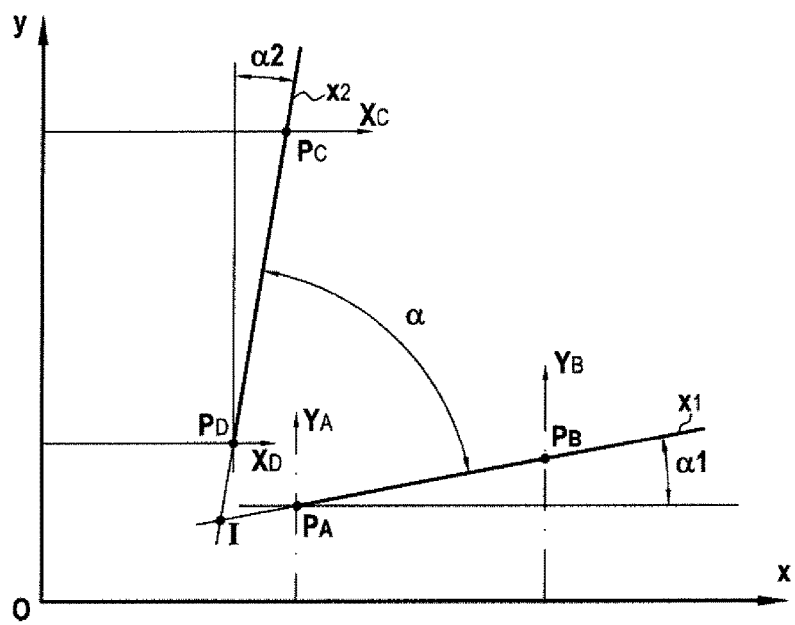
FIG. 5 is a diagram illustrating the principle of the invention according to a second alternative embodiment.

According to a second alternative embodiment, the angle α is defined between the first segment $x_1$ and the second segment $x_2$ which passes through the third PC and fourth PD measuring points, with the fourth measuring point PD being located on the vertical wall 4, in proximity to the base 3, i.e. in proximity to the heel 9 of the container 2 (FIG. 5). According to this alternative embodiment, the third measuring point PC may be located at different levels of the vertical wall 4. According to this second alternative, the segments $x_1$ and $x_2$ intersect at an intersection point I.

This quantity depending on the angle α is calculated for each rotational position or increment of the container 2 and this for at least one revolution of the container 2 on itself. From variations of this quantity over at least one revolution of the container 2, the processing and calculation unit 12 measures the verticality of the container 2.

The taking into account of two points PA and PB on the base of the container 2 and of at least one point PC on the vertical wall 4 of the container leads to the formation of an angle α which is characteristic of the verticality of the container 2. Thus, it is considered that this angle α should remain constant during the whole rotation of the container so that the position variations of the points PA, PB, PC or PD or the deformations of this angle α are representative or proportional to the verticality of the container 2.

The object of the invention therefore aims at selecting a quantity which depends on this angle α so that the variations of this quantity allow measurement of the verticality. In other words, by analyzing the changes in the quantity depending on this angle α, it is possible to infer the measurement of verticality therefrom. The measurement of the verticality is thus calculated as being the deviation between the maximum value and the minimum value of the quantity depending on this angle α. According to an advantageous embodiment feature, the determination of the measurement of the verticality is carried out after an operation for filtering the values of the quantity depending on the angle α. This filtering operation aims at suppressing the variations of the quantity depending on the angle α, those corresponding for example to other geometrical deformations of a container such as its ovalization or a distorted base, to a local defect of its wall such as a bump or a recess, to imperfections due to the handling of the container during its rotation. The operation for filtering the variations of the quantity may for example be a frequency breakdown of the recorded measurements considered as a one-dimensional signal of the time t or of the angle of rotation θ, in order to retain after filtering, exclusively the frequency component equal to that of the verticality i.e. the one corresponding to a revolution of the container on itself. Of course, there exist different solutions for selecting the quantity depending on this angle α, notably depending on the desired expression for the verticality. Generally, and as recalled in the preamble of the description, the verticality of a container is expressed in various ways and in particular either in an angle unit such as degrees or in a unit of length such as millimeters.

For example, as a quantity depending on the angle α, the deviation between the angle $α_1$ and $α_2$ or the deviation of the tangents of the angle $α_1$ and $α_2$ may be selected.

According to the example illustrated in FIG. 3, the angle $α_1$ is the tilt angle between the segment $x_1$ passing through the first measuring point PA and the second measuring point PB on the one hand and the segment parallel to the first axis x of the orthonormal reference system (0, x, y) on the other hand. Also, the angle $α_2$ is the tilt angle between the segment $x_2$ passing through the first measuring point PA and the third measuring point PC on the one hand and the segment parallel to the second axis y of the orthonormal reference system (0, x, y) on the other hand.

According to the example illustrated in FIG. 5, the angle $α_1$ is the tilt angle between the segment $x_1$ passing through the first measuring point PA and the second measuring point PB on the one hand and the segment parallel to the first axis x of the orthonormal reference system (0, x, y) on the other hand. Also, the angle $α_2$ is the tilt angle between the segment $x_2$ passing through the third measuring point PC and the fourth measuring point PD on the one hand and the segment parallel to the second axis y of the orthonormal reference system (0, x, y) on the other hand.

Thus, for example the calculation of tan ($α_1$) corresponds to the difference between the coordinates or positions of the points PB and PA along the y axis, divided by the distance D separating both sensors A and B. In the same way, the calculation of tan ($α_2$) corresponds for the example illustrated in FIG. 3, to the difference between the coordinates or positions of the points PC and PA along the x axis, divided by the distance HC separating both sensors A and C. The calculation of tan ($x_2$) corresponds for example as illustrated in FIG. 5, to the difference between the coordinates or positions of the third and fourth points PC and PD along the x axis, divided by the distance separating the third PC and fourth PD sensors.

It should be noted that the positions of the measuring points PA to PC may be referenced to a zero value.

Figure 4:
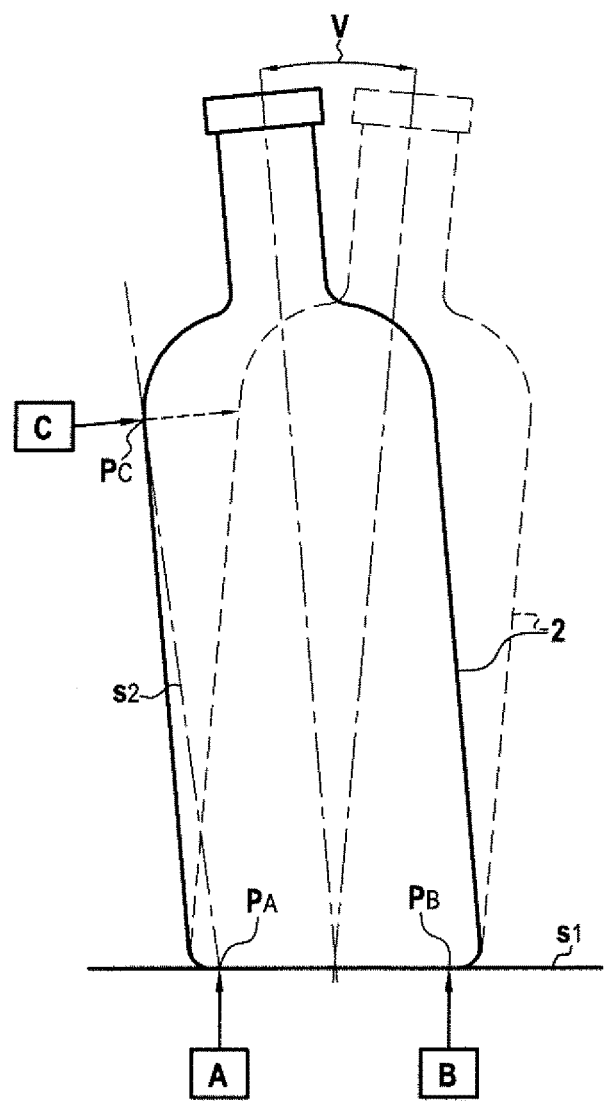
FIG. 4 is a diagram with which the measurement of verticality according to the invention may be illustrated.
Figure 6:
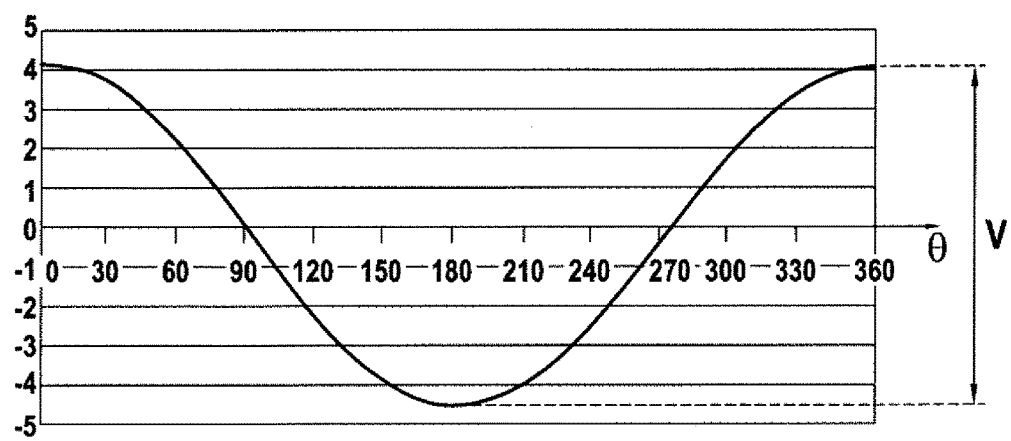
FIG. 6 is a curve illustrating an example of variation of the values of the quantity depending on the angle α according to the angle of rotation θ of the container.

The deviation between tan ($\alpha_1$) and tan ($\alpha_2$) is calculated for each rotational increment. The measurement of the verticality V corresponds to the difference between the maximum value and the minimum value of this deviation calculated for the various positions of the container taken over one revolution (FIG. 4). FIG. 6 illustrates according to the angle of rotation θ over 360°, the variations of the value of the quantity depending on the angle α. The measurement of the verticality V corresponds to the difference between the maximum value and the minimum value of the quantity depending on the angle α.

According to an alternative embodiment, this measurement of verticality is compared with a reference or comparison value in order to determine the presence of a lack of verticality. Thus, if the measurement of verticality is less than this reference value, the container is considered as non-faulty while if the measurement of verticality is greater than this reference value, the container is considered as having a lack of verticality.

It emerges from the preceding description that the invention allows measurement of the actual verticality of containers since the measurement principle is independent of the axis of rotation of the inspection station. Taking into account at least two measuring points on the base of the container and of at least one measuring point on the vertical wall 4 on the container allows an angle α to be defined between two segments $x_1$, $x_2$, the variations of which are characteristic of the verticality of the container. It should be noted that both of these secant segments $x_1$ and $x_2$ form the two sides of a triangle, the deformations of which are also representative of the verticality of the container 2 (the third side of the triangle being formed by the segment passing through the second PB and third PC measuring point).

In the preceding description, the angle α is defined by applying three sensors (FIG. 3) or four sensors (FIG. 5). It should be noted that the alternative illustrated in FIG. 5 gives the possibility of getting rid of the measurement errors due to translation of the container 2 along the first axis x of the reference system (0, x, y).

Of course, the measurement of verticality may be conducted at any level of the vertical wall 4 (with the sensor C). Also, it may be advantageous to measure the verticality at two different heights, for example at a measuring point located on the body 5 as far as possible from the base 3 like in proximity to the shoulder 7, and at a measuring point located on the ring 8. The processing and calculation unit 12 thus calculates, as explained above, for each rotational position of the container 2, a quantity depending on an angle α with a measuring point located on the body 5 in proximity to the shoulder 7 and a quantity depending on an angle α with a measuring point located on the ring 8. A verticality measurement of the body and a total verticality measurement may thus be defined. Consequently, a third measurement of verticality of the neck 6 may be defined relatively to the body 5, from the distance between the total and body verticality measurements.

It should be noted that in the case when the angle α is defined between the segment $x_1$ and a segment $x_2$ passing through two different measuring points of the two measuring points through which passes the segment $x_1$ (FIG. 5), the device according to the invention then includes five measurement sensors for conducting this third measurement of verticality. Thus, according to this alternative, the device includes two sensors A and B for the two measuring points located on the base 3, two sensors C and D for the two measurements points respectively located in proximity to the shoulder 7 and to the heel 9 for measuring the body verticality, and a fifth sensor not shown for a measuring point located on the ring 8 allowing measurement of the total verticality in combination with the sensor D. This fifth sensor has the same characteristics as those described earlier for the fourth sensor D for the measurement located at the ring 8.

In the preceding description, it is considered that the vertical wall 4 has a cylindrical section at right angles to the measurement axes XC, XD. Under the assumption that the vertical wall 4 is not strictly vertical, adapting the operation and/or the position of the sensors C and D may be contemplated. Under the assumption of containers 2 with a non-circular, for example oval, elliptical or polygonal section, provision may be made, from the theoretical geometry of the article, for predicting the normal deformations of the angle α during the rotation of the container 2 and for inferring therefrom a measurement of verticality from the deviations between the normal deformations of the angle α and the measured deformations.

The invention is not limited to the described and illustrated examples since various modifications may be made thereto without departing from the scope thereof.

The invention claimed is:

1. A method for measuring the verticality of a container (2) having a base (3) from which rises a vertical wall (4) exhibiting a body 5, the method consisting of rotating the container (2) on itself over at least one revolution by a driving system (13) comprising a supporting plane (14) for the base (3) and the body (5) and a wheel (16) for driving into container secured by the body (5) bearing on two abutments (17) during rotation and of conducting, during the rotation of the container, measurements at different rotational positions of the container, the method comprising:
   measuring at each rotational position of the container (2), at least:
   the position along a first measurement axis (YA), of at least one first measuring point (PA) located on the base (3) and situated on or outside of the supporting plane (14),
   the position along a second measurement axis (YB), of a second measuring point (PB) located on the base (3) diametrically opposite to the first measuring point,
   the position along a third measurement axis (XC), of at least one third measuring point (PC) located on the vertical wall (4) at a distance from the base (3), the first, second and third measurement axes being coplanar in a measurement plane (P),
   selecting an angle (a) defined between a first segment ($x_1$) passing through the first (PA) and second (PB) measuring points and a second segment ($x_2$) intersecting the first segment and passing through at least the third measuring point (PC) so that the variation of this angle is representative of the verticality of the container (2),
   calculating for each rotational position of the container (2), a quantity depending on the angle (α),
   and measuring the verticality considered over at least one revolution of the container by calculating the difference between a maximum value and a minimum value of the quantity depending on the angle ($\alpha$).

2. The method according to claim 1, further comprising measuring the verticality, after an operation for filtering the variations of the quantity depending on the angle ($\alpha$).

3. The method according to claim 1, further comprising selecting the angle ($\alpha$) defined between the first segment and the second segment ($x_2$) passing through the third measuring point (PC) and the first measuring point (PA).

4. The method according to claim 1, further comprising measuring at each rotational position of the container (2), the position along at least one fourth measurement axis (XD) coplanar with the first (YA), second (YB) and third (XC) measurement axes, of at least one fourth measuring point (PD) located on the vertical wall (4) of the container in different locations of the third measuring point (PC).

5. The method according to claim 4, further comprising selecting the position of the third (PC) measuring point on the vertical wall (4) located on the body (5) as far as possible from the base, and the position of the forth (PD) measuring point on a ring (8) of the container, so as to define an angle (a) defined between the first segment and the second segment passing through the third (PC) and first (PA) measuring points, and another angle (a) defined between the first segment and a third segment passing through the fourth (PD) and first (PA) measuring points allowing definition of a measurement of verticality of the body for the point located on the body (5) and the a measurement of total verticality for the point located on the ring (8).

6. The method according to claim 5, further comprising determining a measurement of verticality of the neck (6) relatively to the body (5) from the difference between the total and body verticality measurements.

7. The method according to claim 4, further comprising selecting at least one angle (a) defined between the first segment ($x_1$) and the second segment ($x_2$) passing through the third measuring point (PC) and the fourth measuring point (PD) located in proximity to a heel (9) of the container.

8. The method of claim 7, further comprising selecting the position of the third measuring point (PC) on the body (5) as far as possible from the base for determining a measurement of body verticality and of selecting the position of a fifth measuring point on a ring (8) of the container so as to define another angle (a) defined between the first segment ($x_1$) and a third segment passing through the fourth (PD) and fifth measuring points allowing definition of a measurement of total verticality.

9. The method according to claim 4, wherein the position is along a fifth measurement axis coplanar with the first (YA), second (YB) and third (XC) measurement axes, of a fifth measuring point located on the vertical wall (4) of the container in different locations of the third measuring point (PC).

10. The method according to claim 1, further comprising calculating, for each rotational position of the container, as a quantity depending on the angle (a), a deviation between an angle $a_1$ and an angle $a_2$ or a deviation between tangents of the angles $a_1$ and $a_2$;
wherein the angle (a) is defined by the first (PA), second (PB) and third (PC) measuring points, or defined by the first (PA), second (PB), and a fourth (PD) measuring point, or the first (PA), second (PB), third (PC), and fourth (PD) measuring points; and
wherein $a_1$ is a tilt angle between the segment passing through the first (PA) and second (PB) measuring points and a segment parallel to a first axis (x) parallel to the third measurement axis (XC) and being part of an orthonormal reference system (0, x, y) located in the measurement plane (P), and
$a_2$ is a tilt angle between the segment either passing through the first (PA) and third (PC) or fourth (PD) measuring points or through the third (PC) and fourth (PD) measuring points and a segment parallel to a second axis (y) parallel to the first (YA) and second (YB) measurement axes and being part of the orthonormal reference system (0, x, y).

11. The method according to claim 1, further comprising referencing to a zero value, the positions measured by sensors (A to D).

12. The method according to claim 1, characterized in further comprising comparing the verticality measurement with a reference value for determining the presence of a lack of verticality or not.

13. The method according to claim 1, further comprising measuring the position of the different measuring points by means of sensors in contact or without any contact with the container.

14. The method according to claim 13, further comprising measuring the position of the different measuring points by means of contactless sensors of the optical type.

15. A device for measuring the verticality on containers (2) having a base (3) from which rises a vertical wall (4) exhibiting a body 5, each container being driven into rotation on itself according to at least one revolution by a driving system (13) comprising a supporting plane (14) for the base (3) and the body (5) and a wheel (16) for driving into rotation the container secured by the body (5) bearing on two abutments (17) during rotation, the device including a measurement system (11) connected to a processing and calculation unit (12), characterized in that:
the measurement system (11) includes at least three measurement sensors (A, B, C) suitable for measuring the position along first (YA), second (YB) and third (XC) measurement axes coplanar with each other, respectively of first (PA), second (PB) and third (PC) measuring points, the first (PA) and second (PB) measuring points being located on the base (3) of the container diametrically opposite to each other while the third measuring point (PC) is located on the vertical wall (4) at a distance from the base (3),
the processing and calculation unit (12) includes means for calculating, for each rotational position of the container (2), a quantity depending on an angle ($\alpha$) defined between a first segment passing through the first (PA) and second (PB) measuring points and a second segment intersecting the first segment and passing through at least the third measuring point (PC) so that the variation of this angle is representative of the verticality of the container (2), this processing and calculation unit (12) including means for determining a verticality measurement by calculating the difference between a maximum value and a minimum value of the quantity depending on the angle ($\alpha$).

16. The device according to claim 15, wherein the measurement system (11) includes at least one fourth measurement sensor (D) suitable for measuring the position, at each rotational position of the container (2), along a fourth measurement axis (XD) coplanar with the first (YA), second (YB) and third (XC) measurement axis, of a fourth (PD) measuring point located on the vertical wall (4) of the container and in that the processing and calculation unit (12) includes means for calculating, for each rotational position of the container (2), a quantity depending on at least one angle ($\alpha$) defined by the first segment and the second segment either passing through the third (PC) and first (PA) measuring points or through the third (PC) and fourth (PD) measuring points, the processing and calculation unit (12) including means for determining at least one measurement of verticality from the variations of the quantity depending on this angle.

17. The device according to claim 15, wherein the sensors (A, B, C, D) are contactless sensors of the optical type.

\* \* \* \* \*